United States Patent

Sirrenberg et al.

[11] 4,139,636
[45] Feb. 13, 1979

[54] N-PHENYL-N'-BENZOYL-UREAS AND PESTICIDAL COMPOSITIONS AND USES THEREFOR

[75] Inventors: Wilhelm Sirrenberg, Sprockhoevel; Erich Klauke, Odenthal; Ingeborg Hammann, Cologne; Wilhelm Stendel, Wuppertal, all of Fed. Rep. of Germany

[73] Assignee: Bayer Aktiengesellschaft, Leverkusen, Fed. Rep. of Germany

[21] Appl. No.: 882,295

[22] Filed: Feb. 27, 1978

Related U.S. Application Data

[63] Continuation of Ser. No. 755,903, Dec. 30, 1976, abandoned.

[30] Foreign Application Priority Data

Jan. 20, 1976 [DE] Fed. Rep. of Germany ....... 2601780

[51] Int. Cl.² .......... A01N 9/12; A01N 9/20; C07C 127/00
[52] U.S. Cl. ................ 424/322; 260/553 A; 260/553 E
[58] Field of Search .......... 424/322; 260/553 A, 260/553 E

[56] References Cited

U.S. PATENT DOCUMENTS

| 3,748,356 | 7/1973 | Wellinga et al. | 424/322 |
| 3,992,553 | 11/1976 | Sirrenberg et al. | 424/322 |
| 4,005,223 | 1/1977 | Sirrenberg et al. | 424/322 |
| 4,041,177 | 8/1977 | Sirrenberg et al. | 424/322 |
| 4,085,226 | 4/1978 | Sirrenberg et al. | 424/322 |

FOREIGN PATENT DOCUMENTS 2123236  2/1971  Fed. Rep. of Germany.

OTHER PUBLICATIONS

Chem. Abst. 71, 36617(m), (1969), Zakaria et al.

Primary Examiner—Albert T. Meyers
Assistant Examiner—D. W. Robinson
Attorney, Agent, or Firm—Sprung, Felfe, Horn, Lynch & Kramer

[57] ABSTRACT

N-phenyl-N'-benzoyl-ureas of the formula

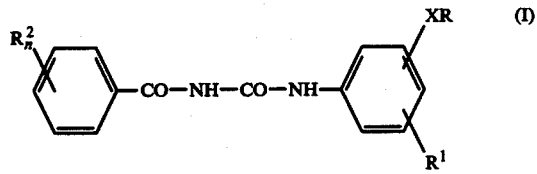

in which
  R represents halogenoalkyl with 1 to 4 carbon atoms,
  $R^1$ represents hydrogen or halogen,
  $R^2$ represents halogen, nitro, alkyl with 1 to 3 carbon atoms or alkoxy with 1 to 3 carbon atoms,
  X represents an oxygen atom or sulfur atom, and
  n denotes 0, 1, 2, 3, 4 or 5;
which possess arthropodicidal properties.

10 Claims, No Drawings

N-PHENYL-N'-BENZOYL-UREAS AND PESTICIDAL COMPOSITIONS AND USES THEREFOR

This is a continuation of application Ser. No. 755,903, filed Dec. 30, 1976, now abandoned.

The present invention relates to and has for its objects the provision of particular new N-phenyl-N'-benzoyl-ureas which possess arthropodicidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from German Published Specification DOS No. 2,123,236 that certain benzoylureas, such as, for example, N-(2,6-dichlorobenzoyl)-N'-(4-chloro-(Compound A) or 3,4-dichloro-phenyl)-urea, (Compound B) possess insecticidal properties.

The present invention now provides, as new compounds, the N-phenyl-N'-benzoylureas of the general formula $$R_n^2\text{—C}_6\text{H}_3\text{—CO—NH—CO—NH—C}_6\text{H}_3(R^1)(XR) \quad (I)$$

in which
  R represents halogenoalkyl with 1 to 4 carbon atoms,
  $R^1$ represents hydrogen or halogen,
  $R^2$ represents halogen, nitro, alkyl with 1 to 3 carbon atoms or alkoxy with 1 to 3 carbon atoms,
  X represents an oxygen atom or sulfur atom, and
  $n$ denotes 0, 1, 2, 3, 4 or 5.

Preferably, R represents straight-chain or branched halogenoalkyl with 1 to 3 (especially 1 or 2) carbon atoms, $R^1$ represents hydrogen or chlorine, $R^2$ represents nitro, fluorine, chlorine, bromine, iodine, methyl, ethyl, methoxy or ethoxy and $n$ represents 0, 1, 2 or 3.

Surprisingly, the N-phenyl-N'-benzoylureas according to the invention have a substantially better insecticidal action than the nearest compounds of analogous structure and of the same type of action, previously known from the state of the art. The compounds according to the invention thus represent a genuine enrichment of the art.

The present invention also provides a process for the preparation of an N-phenyl-N'-benzoylurea of the formula (I) in which (a) a substituted aniline of the general formula $$RX\text{—C}_6\text{H}_3(R^1)\text{—NH}_2 \quad (II)$$

is reacted with a benzoylisocyanate of the general formula $$R_n^2\text{—C}_6\text{H}_3\text{—CO—NCO} \quad (III),$$

in which formulas
  R, $R^1$, $R^2$, X and $n$ have the above-mentioned meanings, if appropriate in the presence of a diluent or solvent, or (b) a substituted phenylisocyanate of the general formula $$RX\text{—C}_6\text{H}_3(R^1)\text{—NCO} \quad (IV)$$

is reacted with a benzamide of the general formula $$R_n^2\text{—C}_6\text{H}_3\text{—CO—NH}_2 \quad (V),$$

in which formulas
  R, $R^1$, $R^2$, X and $n$ have the above-mentioned meanings, if appropriate in the presence of a diluent or solvent.

If, following process variant (a), 3-chloro-4-trifluoromethoxyaniline and 2-chlorobenzoylisocyanate are used as starting materials and following process variant (b), 3-chloro-4-trifluoromethoxyphenylisocyanate and 2,6-difluorobenzamide are used as starting materials, the course of the reactions can be represented by the following equations:

$$F_3CO\text{—C}_6H_3(Cl)\text{—NH}_2 + \text{Cl—C}_6H_4\text{—CO—NCO}$$
$$(IIa) \quad (IIIa)$$

$$\longrightarrow F_3CO\text{—C}_6H_3(Cl)\text{—NH—CO—NH—CO—C}_6H_4(Cl)$$
$$(30)$$

$$F_3CO\text{—C}_6H_3(Cl)\text{—NCO} + F\text{—C}_6H_3(F)\text{—CO—NH}_2$$
$$(IVa) \quad (Va)$$

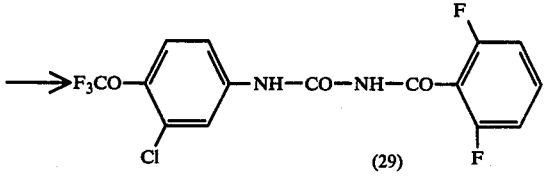

Substituted anilines (II) to be used as starting materials are known and can be prepared in accordance with processes known from the literature (see for example, J.Org.Chem. 25, (1960), 965 and 29, (1964), 1; Am. Soc. 73, (1951), 5831; Bull. Soc. Chim. France 4, (1957), 531; Z. obsc.Chim. 35, (1965), 1377 English translation; Am. Soc. 83 (1961), 4360 and U.S. Patent Specification 3,387,037); the amino group can be converted to the isocyanate group in accordance with customary processes, for example by reaction with phosgene, whereby the corresponding phenylisocyanates (IV) are obtained.

The following may be mentioned as individual examples: 4-trifluoromethoxy-, 4-trifluoromethylthio-, 3-trifluoromethoxy-, 3-trifluoromethylthio-, 2-trifluoromethoxy-, 2-trifluoromethylthio-, 3-chloro-4-trifluoromethoxy-, 3-chloro-4-trifluoromethylthio-, 4-difluoromonochloromethylthio, 3-chloro-4-difluoromonochloromethylthio-, 2-chloro-4-difluoromonochloromethylthio-, 4-(2-chloro-1,1,2-trifluoro-ethoxy)- and 3-chloro-4-(2-chloro-1,1,2-trifluoro-ethoxy)-anilines or -phenylisocyanates.

The benzoylisocyanates (III) also to be used as starting materials are known (see J.Org.Chem. 30 (12), pages 4,306–4,307 (1965)), as are the benzamides (V) (see Beilstein "Handbuch der organischen Chemie" ("Handbook of Organic Chemistry"), volume 9, page 336).

The following may be mentioned as individual examples: 2-methyl-, 2-ethyl-, 3-methyl-, 3-ethyl-, 4-methyl-, 4-ethyl-, 2-chloro-, 4-chloro-, 2,4-dichloro-, 2,4-difluoro-, 2,6-dichloro-, 2,6-difluoro-, 2-fluoro-, 2-bromo-, 2-iodo-, 2-nitro-, 3-nitro-, 4-nitro-, 2-methoxy-, 2-ethoxy- and 2,3,6-trichlorobenzoylisocyanates or -benzamides.

The process for the preparation of the N-phenyl-N'-benzoyl-ureas according to the invention is preferably carried out in the presence of a suitable solvent or diluent. Virtually all inert organic solvents can be used for this purpose, especially aliphatic and aromatic, optionally chlorinated, hydrocarbons, such as benzene, toluene, xylene, benzine, methylene chloride, chloroform, carbontetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

The reaction temperature can be varied within a fairly wide range. In general, the reaction is carried out at between 0° and 120° C and preferably at 70°–85° C.

The reaction is in general allowed to take place under normal pressure.

To carry out the process, the starting components are preferably employed in equimolar amounts. An excess of one or other reactant produces no essential advantages.

In general, the reactants are brought together in one of the stated solvents. The substituted phenylisocyanates (IV) to be employed in process variant (b) can be employed as such or, without interim isolation, in the form of their reaction mixture obtained after the reaction of amine and phosgene. Preferably, the benzamide (V) is added to this reaction mixture contained in one of the above-mentioned solvents.

The reactions are usually carried out under the above-mentioned conditions and the products which separate out are isolated in the usual manner by filtration, washing and, if appropriate, recrystallization.

The compounds are obtained in a crystalline form having a sharp melting point.

As already mentioned, the N-phenyl-N'-benzoylureas according to the invention are distinguished by an excellent insecticidal activity. They are not only active against plant pests but also, in the veterinary medicine field, against animal parasites (ectoparasites), such as parasitic fly larvae. For this reason, the compounds according to the invention can be employed successfully as pesticides in plant protection and in the veterinary field.

The active compounds are well tolerated by plants, have a favorable level of toxicity to warm-blooded animals, and can be used for combating arthropod pests, especially insects, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera* spec.; from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locustria migratoria migratorioides, Melanoplus differentialis* and *Schistocerca gregaria;* from the order of the Dermaptera, for example *Forficula auricularia;* from the order of the Isoptera, for example Reticulitermes spp.; from the order of the Anoplura, for example *Phylloxera vastatrix,* Pemphigus spp., *Pediculus humanus corporis,* Haematopinus spp. and Linognathus spp.; from the order of the Mallophaga, for example Trichodectes spp. and Damalinea spp.; from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.; from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasea spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.; from the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.; from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example, Xenopsylla cheopis and Ceratophyllus spp..

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins, (e.g. petroluem or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agnets, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides, or nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

In the veterinary field, the active compounds according to the invention are used in a known manner, such as by oral use in the form of, for example, tablets, capsules, drenches or granules, by dermal use by means of, for example, dipping, spraying, pouring-on, spotting-on and powdering, and by parenteral use by means of, for example, injections.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Phaedon larvae test

Solvent: 15 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dripping wet and were then infested with mustard beetle larvae (*Phaedon cochleariae*).

After the specified periods of time, the degree of destruction was determined in %: 100% meant that all beetle larvae had been killed, whereas 0% meant that none of the beetle larvae had been killed.

The active compounds, the concentrations of the active compounds, the evaluation times and the results can be seen from the following table.

Table 1
(Insects which damage plants)
*Phaedon* larvae test

| Active compounds | Active compound concentration in % | Degree of destruction in % after 3 days |
|---|---|---|
| 2,6-dichloro-phenyl—CO—NH—CO—NH—phenyl(Cl) with additional Cl (known) (A) | 0.1<br>0.01<br>0.001 | 100<br>30<br>0 |
| 2,6-dichloro-phenyl—CO—NH—CO—NH—2,4-dichloro-phenyl (known) (B) | 0.1<br>0.01<br>0.001 | 100<br>15<br>0 |
| 2-chloro-phenyl—CO—NH—CO—NH—phenyl-OCF$_3$ | 0.1<br>0.01<br>0.001 | 100<br>100<br>95 |

(58)

Table 1-continued
(Insects which damage plants)
Phaedon larvae test

| Active compounds | Active compound concentration in % | Degree of destruction in % after 3 days |
|---|---|---|
| 2,6-F,F-C₆H₃-CO-NH-CO-NH-C₆H₄-OCF₃ (61) | 0.1<br>0.01<br>0.001 | 100<br>100<br>100 |
| 2,6-F,F-C₆H₃-CO-NH-CO-NH-C₆H₄-SCF₃ (10) | 0.1<br>0.01<br>0.001 | 100<br>100<br>100 |
| 2-Cl-C₆H₄-CO-NH-CO-NH-(3-Cl,4-SCF₃)C₆H₃ (40) | 0.1<br>0.01<br>0.001 | 100<br>100<br>80 |
| 2,6-F,F-C₆H₃-CO-NH-CO-NH-(3-Cl,4-SCF₃)C₆H₃ (44) | 0.1<br>0.01<br>0.001 | 100<br>100<br>100 |
| 2-Cl-C₆H₄-CO-NH-CO-NH-(3-Cl,4-OCF₃)C₆H₃ (30) | 0.1<br>0.01<br>0.001 | 100<br>100<br>90 |
| 2-Br-C₆H₄-CO-NH-CO-NH-(3-Cl,4-OCF₃)C₆H₃ (33) | 0.1<br>0.01<br>0.001 | 100<br>100<br>80 |
| 2,6-F,F-C₆H₃-CO-NH-CO-NH-(3-Cl,4-OCF₃)C₆H₃ (29) | 0.1<br>0.01<br>0.001 | 100<br>100<br>100 |
| 2-Cl-C₆H₄-CO-NH-CO-NH-(3-Cl,4-SCF₂Cl)C₆H₃ (78) | 0.1<br>0.01<br>0.001 | 100<br>100<br>90 |
| 2,6-Cl,Cl-C₆H₃-CO-NH-CO-NH-(3-Cl,4-SCF₂Cl)C₆H₃ (79) | 0.01<br>0.01<br>0.001 | 100<br>100<br>65 |
| 2-Br-C₆H₄-CO-NH-CO-NH-(3-Cl,4-SCF₂Cl)C₆H₃ (75) | 0.1<br>0.01<br>0.001 | 100<br>100<br>80 |

Table 1-continued (Insects which damage plants)
Phaedon larvae test

| Active compounds | Active compound concentration in % | Degree of destruction in % after 3 days |
|---|---|---|
| (76) 2,6-F₂-C₆H₃-CO-NH-CO-NH-C₆H₃(Cl)-SCF₂Cl | 0.1<br>0.01<br>0.001 | 100<br>100<br>85 |
| (21) 2-Cl-C₆H₄-CO-NH-CO-NH-C₆H₃(Cl)-OCF₂-CHFCl | 0.1<br>0.01<br>0.001 | 100<br>100<br>85 |
| (19) 2-Br-C₆H₄-CO-NH-CO-NH-C₆H₃(Cl)-OCF₂-CHFCl | 0.1<br>0.01<br>0.001 | 100<br>100<br>65 |
| (18) 2,6-F₂-C₆H₃-CO-NH-CO-NH-C₆H₃(Cl)-OCF₂-CHFCl | 0.1<br>0.01<br>0.001 | 100<br>100<br>80 |

EXAMPLE 2

Plutella test

Solvent: 15 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (Brassica oleracea) were sprayed with the preparation of the active compound until dew moist and were then infested with caterpillars of the diamond-back moth (Plutella maculipennis).

After the specified periods of time, the degree of destruction was determined as a percentage: 100% meant that all the caterpillars were killed, whereas 0% meant that none of the caterpillars were killed.

The active compounds, the concentrations of the active compounds, the evaluation times and the results can be seen from the following table:

(Insects which damage plants)
Plutella test

| Active compounds | Active compound concentration in % | Degree of destruction in % after 7 days |
|---|---|---|
| 2,6-Cl₂-C₆H₃-CO-NH-CO-NH-C₆H₄-Cl<br>(known) (A) | 0.1<br>0.01 | 65<br>0 |
| (58) 2-Cl-C₆H₄-CO-NH-CO-NH-C₆H₄-OCF₃ | 0.1<br>0.01 | 100<br>100 |
| (59) 2,6-Cl₂-C₆H₃-CO-NH-CO-NH-C₆H₄-OCF₃ | 0.1<br>0.01 | 100<br>100 |

-continued (Insects which damage plants)

*Plutella* test

| Active compounds | Active compound concentration in % | Degree of destruction in % after 7 days |
|---|---|---|
| (62) 2-Br-C6H4-CO-NH-CO-NH-C6H4-OCF3 | 0.1<br>0.01 | 100<br>100 |
| (60) 2-F-C6H4-CO-NH-CO-NH-C6H4-OCF3 | 0.1<br>0.01 | 100<br>100 |
| (61) 2,6-F2-C6H3-CO-NH-CO-NH-C6H4-OCF3 | 0.1<br>0.01 | 100<br>100 |
| (10) 2,6-F2-C6H3-CO-NH-CO-NH-C6H4-SCF3 (para) | 0.1<br>0.01 | 100<br>100 |
| (2) 2,6-F2-C6H3-CO-NH-CO-NH-C6H4-SCF3 (meta) | 0.1<br>0.01 | 100<br>100 |
| (40) 2-Cl-C6H4-CO-NH-CO-NH-(3-Cl,4-SCF3)C6H3 | 0.01<br>0.01 | 100<br>100 |
| (39) 2,6-Cl2-C6H3-CO-NH-CO-NH-(3-Cl,4-SCF3)C6H3 | 0.1<br>0.01 | 100<br>100 |
| (42) 2-Br-C6H4-CO-NH-CO-NH-(3-Cl,4-SCF3)C6H3 | 0.1<br>0.01 | 100<br>100 |
| (30) 2-Cl-C6H4-CO-NH-CO-NH-(3-Cl,4-OCF3)C6H3 | 0.1<br>0.01 | 100<br>100 |
| (33) 2-Br-C6H4-CO-NH-CO-NH-(3-Cl,4-OCF3)C6H3 | 0.1<br>0.01 | 100<br>100 |
| (28) 2-F-C6H4-CO-NH-CO-NH-(3-Cl,4-OCF3)C6H3 | 0.1<br>0.01 | 100<br>100 |

-continued (Insects which damage plants)
Plutella test

| Active compounds | Active compound concentration in % | Degree of destruction in % after 7 days |
| --- | --- | --- |
| 2,6-F₂-C₆H₃-CO-NH-CO-NH-C₆H₃(Cl)(OCF₃) (29) | 0.1<br>0.01 | 100<br>100 |
| 2-I-C₆H₄-CO-NH-CO-NH-C₆H₃(Cl)(OCF₃) (32) | 0.1<br>0.01 | 100<br>100 |
| 2-CH₃-C₆H₄-CO-NH-CO-NH-C₆H₃(Cl)(SCF₂Cl) (77) | 0.1<br>0.01 | 100<br>100 |
| 2,6-Cl₂-C₆H₃-CO-NH-CO-NH-C₆H₃(Cl)(SCF₂Cl) (79) | 0.1<br>0.01 | 100<br>100 |
| 2-Br-C₆H₄-CO-NH-CO-NH-C₆H₃(Cl)(SCF₂Cl) (75) | 0.01<br>0.01 | 100<br>100 |
| 2-F-C₆H₄-CO-NH-CO-NH-C₆H₃(Cl)(SCF₂Cl) (74) | 0.1<br>0.01 | 100<br>100 |
| 2,6-F₂-C₆H₃-CO-NH-CO-NH-C₆H₃(Cl)(SCF₂Cl) (76) | 0.1<br>0.01 | 100<br>100 |
| 2-Cl-C₆H₄-CO-NH-CO-NH-C₆H₃(Cl)(OCF₂-CHFCl) (21) | 0.1<br>0.01 | 100<br>100 |
| 2,6-Cl₂-C₆H₃-CO-NH-CO-NH-C₆H₃(Cl)(OCF₂-CHFCl) (20) | 0.1<br>0.01 | 100<br>100 |
| 2-Br-C₆H₄-CO-NH-CO-NH-C₆H₃(Cl)(OCF₂-CHFCl) (19) | 0.1<br>0.01 | 100<br>100 |
| 2,6-F₂-C₆H₃-CO-NH-CO-NH-C₆H₃(Cl)(OCF₂-CHFCl) (18) | 0.1<br>0.01 | 100<br>100 |

-continued (Insects which damage plants)
Plutella test

| Active compounds | Active compound concentration in % | Degree of destruction in % after 7 days |
| --- | --- | --- |
| 2,6-F₂-C₆H₃-CO-NH-CO-NH-C₆H₄-OCF₃ (48) | 0.1<br>0.01 | 100<br>100 |
| 2,4-Cl₂-C₆H₃-CO-NH-CO-NH-C₆H₄-OCF₃ (67) | 0.1<br>0.01 | 100<br>100 |
| 2-I-C₆H₄-CO-NH-CO-NH-C₆H₄-OCF₃ (65) | 0.1<br>0.01 | 100<br>100 |
| 2-CH₃-C₆H₄-CO-NH-CO-NH-(3-Cl,4-OCF₃)C₆H₃ (35) | 0.1<br>0.01 | 100<br>100 |
| 2,4-Cl₂-C₆H₃-CO-NH-CO-NH-(3-Cl,4-OCF₃)C₆H₃ (36) | 0.1<br>0.01 | 100<br>100 |
| 2-Cl-C₆H₄-CO-NH-CO-NH-C₆H₄-SCF₃ (5) | 0.1<br>0.01 | 100<br>100 |
| 2-Br-C₆H₄-CO-NH-CO-NH-C₆H₄-SCF₃ (7) | 0.1<br>0.01 | 100<br>100 |
| 2-CH₃-C₆H₄-CO-NH-CO-NH-C₆H₄-SCF₃ (16) | 0.1<br>0.01 | 100<br>100 |
| 2-Cl-C₆H₄-CO-NH-CO-NH-C₆H₄-SCF₃ (13) | 0.1<br>0.01 | 100<br>100 |
| 2,6-Cl₂-C₆H₃-CO-NH-CO-NH-C₆H₄-SCF₃ (12) | 0.1<br>0.01 | 100<br>100 |
| 2-Br-C₆H₄-CO-NH-CO-NH-C₆H₄-SCF₃ (17) | 0.1<br>0.01 | 100<br>100 |

-continued (Insects which damage plants)

Plutella test

| Active compounds | Active compound concentration in % | Degree of destruction in % after 7 days |
|---|---|---|
| 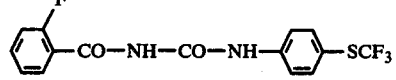 (11) F—C₆H₄—CO—NH—CO—NH—C₆H₄—SCF₃ | 0.1 0.01 | 100 100 |
| 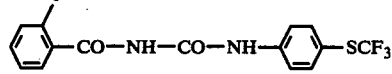 (15) J—C₆H₄—CO—NH—CO—NH—C₆H₄—SCF₃ | 0.1 0.01 | 100 100 |
|  (47) 2,4-Cl₂-C₆H₃—CO—NH—CO—NH—(3-Cl-C₆H₃)—SCF₃ | 0.1 0.01 | 100 100 |
| 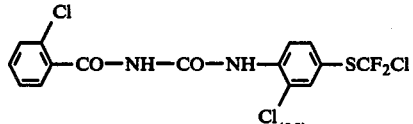 (85) 2,6-Cl₂-C₆H₃—CO—NH—CO—NH—(3-Cl-C₆H₃)—SCF₂Cl | 0.1 0.01 | 100 100 |
| 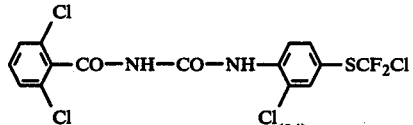 (84) 2,6-Cl₂-C₆H₃—CO—NH—CO—NH—(3-Cl-C₆H₃)—SCF₂Cl | 0.1 0.01 | 100 100 |
| 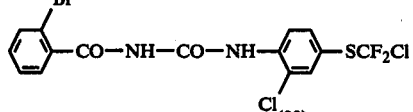 (88) 2-Br-C₆H₄—CO—NH—CO—NH—(3-Cl-C₆H₃)—SCF₂Cl | 0.1 0.01 | 100 100 |
| 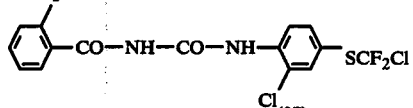 (87) 2-F-C₆H₄—CO—NH—CO—NH—(3-Cl-C₆H₃)—SCF₂Cl | 0.1 0.01 | 100 100 |
| 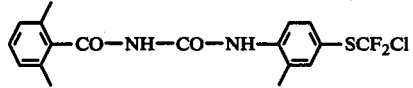 (83) 2,6-F₂-C₆H₃—CO—NH—CO—NH—(3-Cl-C₆H₃)—SCF₂Cl | 0.1 0.01 | 100 100 |
|  (22) 2-F-C₆H₄—CO—NH—CO—NH—(3-Cl-C₆H₃)—OCF₂—CHFCl | 0.1 0.01 | 100 100 |
|  (43) 2-F-C₆H₄—CO—NH—CO—NH—(3-Cl-C₆H₃)—SCF₃ | 0.1 0.01 | 100 100 |
|  (44) 2,6-F₂-C₆H₃—CO—NH—CO—NH—(3-Cl-C₆H₃)—SCF₃ | 0.1 0.01 | 100 100 |

-continued

(Insects which damage plants)
Plutella test

| Active compounds | Active compound concentration in % | Degree of destruction in % after 7 days |
|---|---|---|

Structure (J): 2-iodophenyl-CO—NH—CO—NH—(4-SCF₃, 2-Cl-phenyl) — 0.1 / 0.01 — 100 / 100

Structure (41): 2-OCH₃-phenyl-CO—NH—CO—NH—(4-OCF₃, 2-Cl-phenyl) — 0.1 / 0.01 — 100 / 100

Structure (34): 2-Cl-phenyl-CO—NH—CO—NH—(4-S—CF₂Cl, 2-Cl-phenyl) — 0.1 / 0.01 — 100 / 100

EXAMPLE 3

Laphygma test

Solvent: 15 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Cotton leaves (*Gossypium hirsutum*) were sprayed with the preparation of the active compound until dew-moist and were then infested with caterpillars of the owlet moth (*Laphygma exigua*).

After the specified periods of time, the destruction in % was determined. 100% meant that all of the caterpillars had been killed, whereas 0% indicated that no caterpillars had been killed.

The active compounds, the concentrations of the active compound, the evaluation times and the results can be seen from the following table:

Table 3

(Insects which damage plants)
Laphygma test

| Active compounds | Active compound concentration in % | Degree of destruction in % after 7 days |
|---|---|---|
| (known) (B): 2,6-diCl-phenyl-CO—NH—CO—NH—(3,4-diCl-phenyl) | 0.001 / 0.0001 / 0.00001 | 100 / 50 / 0 |
| (58): 2-Cl-phenyl-CO—NH—CO—NH—(4-OCF₃-phenyl) | 0.001 / 0.0001 / 0.00001 | 100 / 100 / 100 |
| (59): 2,6-diCl-phenyl-CO—NH—CO—NH—(4-OCF₃-phenyl) | 0.001 / 0.0001 / 0.00001 | 100 / 100 / 100 |
| (62): 2-Br-phenyl-CO—NH—CO—NH—(4-OCF₃-phenyl) | 0.001 / 0.0001 / 0.00001 | 100 / 100 / 95 |
| (61): 2,6-diF-phenyl-CO—NH—CO—NH—(4-OCF₃-phenyl) | 0.001 / 0.0001 / 0.00001 | 100 / 100 / 95 |

Table 3-continued

(Insects which damage plants)

*Laphygma* test

| Active compounds | Active compound concentration in % | Degree of destruction in % after 7 days |
|---|---|---|
| F–C₆H₃(F)–CO—NH—CO—NH—C₆H₄—SCF₃ (10) | 0.001<br>0.0001<br>0.00001 | 100<br>100<br>90 |
| F–C₆H₃(F)–CO—NH—CO—NH—C₆H₄—SCF₃ (2) | 0.001<br>0.0001<br>0.00001 | 100<br>95<br>90 |
| F–C₆H₃(F)–CO—NH—CO—NH—C₆H₃(Cl)—SCF₃ (44) | 0.001<br>0.0001<br>0.00001 | 100<br>100<br>80 |
| Cl–C₆H₄–CO—NH—CO—NH—C₆H₃(Cl)—OCF₃ (30) | 0.001<br>0.0001<br>0.00001 | 100<br>95<br>65 |
| F–C₆H₃(F)–CO—NH—CO—NH—C₆H₃(Cl)—OCF₃ (29) | 0.001<br>0.0001<br>0.00001 | 100<br>100<br>90 |
| Cl–C₆H₃(Cl)–CO—NH—CO—NH—C₆H₃(Cl)—SCF₂Cl (79) | 0.001<br>0.0001<br>0.00001 | 100<br>100<br>80 |
| Br–C₆H₄–CO—NH—CO—NH—C₆H₃(Cl)—SCF₂Cl (75) | 0.001<br>0.0001<br>0.00001 | 100<br>100<br>90 |
| F–C₆H₃(F)–CO—NH—CO—NH—C₆H₃(Cl)—SCF₂Cl (76) | 0.001<br>0.0001<br>0.00001 | 100<br>100<br>85 |
| Cl–C₆H₄–CO—NH—CO—NH—C₆H₃(Cl)—OCF₂—CHFCl (21) | 0.001<br>0.0001<br>0.00001 | 100<br>100<br>100 |
| Cl–C₆H₃(Cl)–CO—NH—CO—NH—C₆H₃(Cl)—OCF₂—CHFCl (20) | 0.001<br>0.0001<br>0.00001 | 100<br>90<br>90 |
| F–C₆H₃(F)–CO—NH—CO—NH—C₆H₃(Cl)—OCF₂—CHFCl (18) | 0.001<br>0.0001<br>0.00001 | 100<br>100<br>100 |

EXAMPLE 4

Test with parasitic fly larvae

Solvent:
- 35 parts by weight of ethylene polyglycol monomethyl ether
- 35 parts by weight of nonylphenol polyglycol ether %

To produce a suitable preparation of active compound, 30 parts by weight of the active substance in question were mixed with the stated amount of solvent which contained the above-mentioned proportion of emulsifier and the concentrate thus obtained was diluted with water to the desired concentration.

30 - 50 fly larvae (*Lucilia cuprina*, resistant) were introduced into a test tube which contained approx. 1 cm³ of horse muscle. 0.5 ml of the preparation of active compound was applied to this horse meat. After 24 hours, the degree of destruction in 5 was determined. 100% meant that all the larvae had been killed and 0% meant that no larvae had been killed.

The active compounds, the concentrations of the active compound and the results can be seen from the following table:

The process of this invention is illustrated by the following preparative examples.

EXAMPLE 5

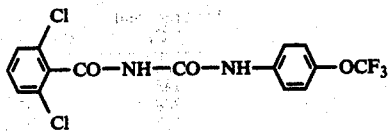
(1)

A solution of 6.5 g (0.03 mole) of 2,6-dichloro-benzoylisocyanate in 20 ml of toluene was added to 5.4 g (0.03 mole) of 4-trifluoromethoxy-aniline dissolved in 80 ml of toluene at 60° C. The batch was stirred for two hours at 80° C, a part of the solvent was distilled off in vacuo and the product which had precipitated was filtered off. After drying, 10 g (84.5% of theory) of analytically pure N-(4-trifluoromethoxyphenyl)-N'-(2,6-dichlorobenzoyl)-urea of melting point 202° C were obtained.

The following compounds were obtained by an analogous procedure:

Table 4

| Active compound | Active compound concentration in ppm | Degree of destruction in % |
|---|---|---|
| (31) 2,6-dichloro-C₆H₃-CO-NH-CO-NH-C₆H₄-OCF₃ | 1,000 / 300 | 100 / 100 |
| (63) C₆H₅-CO-NH-CO-NH-C₆H₄-OCF₃ | 1,000 | 100 |
| (64) 2,4,6-trichloro-C₆H₂-CO-NH-CO-NH-C₆H₄-OCH₃ | 1,000 | 100 |
| (74) 2-F-C₆H₄-CO-NH-CO-NH-(2-Cl-C₆H₃)-SCH₂Cl | 1,000 / 300 | 100 / 100 |
| (18) 2,6-F₂-C₆H₃-CO-NH-CO-NH-(2-Cl-C₆H₃)-OCF₂-CHFCl | 1,000 / 300 / 100 | 100 / 100 / 100 |
| (19) 2-Br-C₆H₄-CO-NH-CO-NH-(2-Cl-C₆H₃)-O-CF₂-CHFCl | 1,000 / 300 / 100 | 100 / 100 / 100 |
| (20) 2,6-Cl₂-C₆H₃-CO-NH-CO-NH-(2-Cl-C₆H₃)-OCF₂-CHFCl | 1,000 | 100 |

Table 5

R²ₙ—⌬—CO—NH—CO—NH—⌬—SCF₃

| Compound No. | R²ₙ | Melting point (°C) | Yield (% of theory) |
|---|---|---|---|
| 2 | 2,6-F | 181 | 75.0 |
| 3 | 2-F | 143 | 44.5 |
| 4 | 2-CH₃ | 208 | 47.0 |
| 5 | 2-Cl | 117 | 58.0 |
| 6 | 2,6-Cl | 213 | 60.5 |
| 7 | 2-Br | 135 | 55.0 |
| 8 | 2,3,6-Cl | 216 | 45.0 |
| 9 | 2-I | 158 | 33.0 |

Table 6

R²ₙ—⌬—CO—NH—CO—NH—⌬—SCF₃

| Compound No. | R²ₙ | Melting point (°C) | Yield (% of theory) |
|---|---|---|---|
| 10 | 2,6-F | 214 | 83.0 |
| 11 | 2-F | 189 | 67.0 |
| 12 | 2,6-Cl | 228 | 77.0 |
| 13 | 2-Cl | 189 | 64.0 |
| 14 | 2,3,6-Cl | 209 | 32.0 |
| 15 | 2-I | 187 | 41.5 |
| 16 | 2-CH₃ | 169 | 41.5 |
| 17 | 2-Br | 190 | 53.0 |

Table 7

R²ₙ—⌬—CO—NH—CO—NH—⌬(Cl)—OCF₂—CHFCl

| Compound No. | R²ₙ | Melting point (°C) | Yield (% of theory) |
|---|---|---|---|
| 18 | 2,6-F | 207 | 90.0 |
| 19 | 2-Br | 192 | 82.5 |
| 20 | 2,6-Cl | 183 | 49.0 |
| 21 | 2-Cl | 187 | 75.0 |
| 22 | 2-F | 187 | 61.0 |
| 23 | 2-CH₃ | 206 | |
| 24 | H | 203 | 61.5 |
| 25 | 2-OCH₃ | 103 | 39.5 |
| 26 | 2,5-Cl | 162 | 61.5 |
| 27 | 2,4-Cl | 179 | 75.5 |

Table 8

R²ₙ—⌬—CO—NH—CO—NH—⌬(Cl)—OCF₃

| Compound No. | R²ₙ | Melting point (°C) | Yield (% of theory) |
|---|---|---|---|
| 28 | 2-F | 161 | 40.0 |
| 29 | 2,6-F | 204–205 | 51.0 |
| 30 | 2-Cl | 194 | 76.0 |
| 31 | 2,6-Cl | 204 | 82.0 |
| 32 | 2-I | 165 | 27.5 |
| 33 | 2-Br | 177 | 68.5 |
| 34 | 2-OCH₃ | 175 | 38.5 |
| 35 | 2-CH₃ | 182 | |
| 36 | 2,4-Cl | 201 | 89.5 |
| 37 | 2,5-Cl | 150 | 58.5 |
| 38 | 2,3,6-Cl | 201.5 | 34.0 |

Table 9

R²ₙ—⌬—CO—NH—CO—NH—⌬(Cl)—SCF₃

| Compound No. | R²ₙ | Melting point (°C) | Yield (% of theory) |
|---|---|---|---|
| 39 | 2,6-Cl | 211 | 71.5 |
| 40 | 2-Cl | 195 | 73.0 |
| 41 | 2-I | 171 | 60.0 |
| 42 | 2-Br | 189 | 59.0 |

Table 9-continued

R²ₙ—⌬—CO—NH—CO—NH—⌬(Cl)—SCF₃

| Compound No. | R²ₙ | Melting point (°C) | Yield (% of theory) |
|---|---|---|---|
| 43 | 2-F | 162 | 81.0 |
| 44 | 2,6-F | 188 | 70.5 |
| 45 | 2-CH₃ | 168 | |
| 46 | all H | 208 | 50.0 |
| 47 | 2,4-Cl | 184 | 86.0 |

Table 10

R²ₙ—⌬—CO—NH—CO—NH—⌬—OCF₃

| Compound No. | R²ₙ | Melting point (°C) | Yield (% of theory) |
|---|---|---|---|
| 48 | 2,6-F | 176 | 92.5 |
| 49 | 2,6-Cl | 200 | 53.5 |
| 50 | 2-Cl | 154 | 58.5 |
| 51 | 2-Br | 150 | 37.0 |
| 52 | 2-CH₃ | 216 | |
| 53 | 2-F | 138 | 68.0 |
| 54 | 2,4-Cl | 146 | 52.5 |
| 55 | all H | 179 | 76.0 |
| 56 | 2-I | 151 | 38.5 |

Table 11

R²ₙ—⌬—CO—NH—CO—NH—⌬—OCF₃

| Compound No. | R²ₙ | Melting point (°C) | Yield (% of theory) |
|---|---|---|---|
| 57 | 2-CH₃ | 190 | 62.0 |
| 58 | 2-Cl | 198 | 88.0 |
| 59 | 2,6-Cl | 202 | 84.5 |
| 60 | 2-F | 181–182 | 58.5 |
| 61 | 2,6-F | 226 | 74.0 |
| 62 | 2-Br | 190 | 74.5 |
| 63 | all H | 225 | 92.5 |
| 64 | 2,3,6-Cl | 163 | 47.0 |
| 65 | 2-I | 176 | 74.0 |
| 66 | 2-OCH₃ | 148 | 37.5 |
| 67 | 2,4-Cl | 176.5 | 84.5 |
| 68 | 2,5-Cl | 166–167 | 87.5 |

Table 12

R²ₙ—⌬—CO—NH—CO—NH—⌬(OCF₃)

| Compound No. | R²ₙ | Melting point (°C) | Yield (% of theory) |
|---|---|---|---|
| 69 | 2,6-F | 172 | 77.0 |
| 70 | 2,6-Cl | 211 | 92.5 |
| 71 | 2-F | 138 | 87.0 |
| 72 | 2-Cl | 137 | 73.5 |
| 73 | 2-Br | 134–135 | 71.0 |

Table 13

R²ₙ—⌬—CO—NH—CO—NH—⌬(Cl)—SCF₃Cl

| Compound No. | R²ₙ | Melting point (°C) | Yield (% of theory) |
|---|---|---|---|
| 74 | 12-F | 153 | 49.0 |
| 75 | 2-Br | 172 | 71.0 |
| 76 | 2,6-F | 185 | 54.5 |
| 77 | 2-CH₃ | 166 | 82.5 |
| 78 | 2-Cl | 182 | 78.5 |
| 79 | 2,6-Cl | 188 | 87.0 |
| 80 | 2,3,6-Cl | 188 | 60.5 |
| 81 | all H | 186 | 85.0 |

Table 13-continued

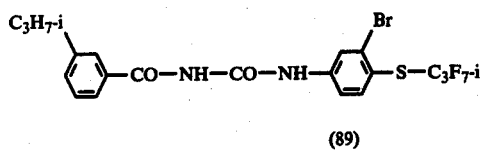

| Compound No. | $R_n^2$ | Melting point (°C) | Yield (% of theory) |
|---|---|---|---|
| 82 | 2-NO$_2$ | 201 | 84.0 |

Table 14

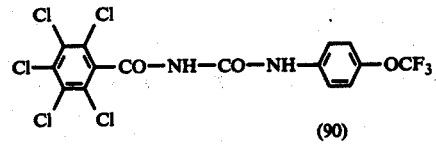

| Compound No. | $R_n^2$ | Melting point (°C) | Yield (% of theory) |
|---|---|---|---|
| 83 | 2,6-F | 193 | 61.0 |
| 84 | 2,6-Cl | 191 | 56.5 |
| 85 | 2-Cl | 191 | 66.0 |
| 86 | 2-CH$_3$ | 165 | |
| 87 | 2-F | 160 | 73.0 |
| 88 | 2-Br | 180 | 49.4 |

Other compounds which can be similarly prepared include:

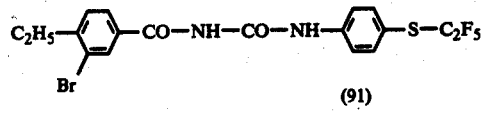

(89)

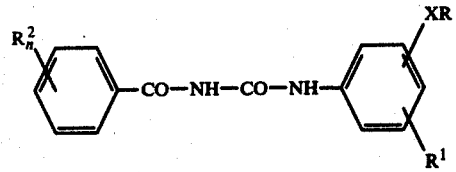

(90)

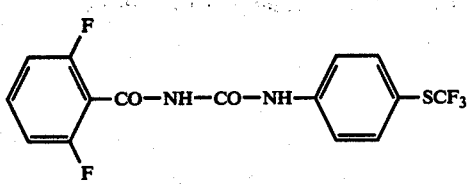

(91)

and the like.

It will be understood that the specification and examples are illustrative but not limitative of the present invention and that other embodiments within the spirit and scope of the invention will suggest themselves to those skilled in the art.

What we claim is:

1. An N-phenyl-N'-benzoylurea of the formula

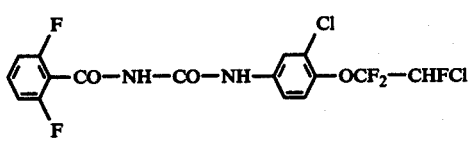

in which
R represents halogenoalkyl with 1 to 4 carbon atoms,
R$^1$ represents hydrogen or halogen,
R$^2$ represents halogen, nitro, alkyl with 1 to 3 carbon atoms or alkoxy with 1 to 3 carbon atoms,
X represents an oxygen atom or sulfur atom, and
n denotes 0, 1, 2, 3, 4 or 5.

2. A urea according to claim 1, in which R represents straight-chain or branched halogenoalkyl with 1 to 3 carbon atoms, R$^1$ represents hydrogen or chlorine, R$^2$ represents nitro, fluorine, chlorine, bromine, iodine, methyl, ethyl, methoxy or ethoxy and n represents 0, 1, 2 or 3.

3. A urea according to claim 1 wherein such compound is N-(4-trifluoromethylthiophenyl)-N'-(2,6-difluorobenzoyl)-urea of the formula

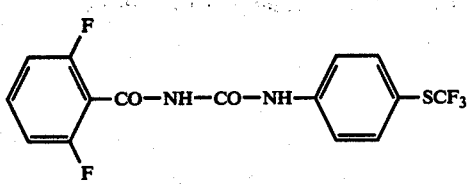

4. A urea according to claim 1 wherein such compound is N-3-[3-chloro-4-(2-chloro-1,1,2-trifluoroethoxy)-phenyl]-N'-(2,6-difluorobenzoyl)-urea of the formula

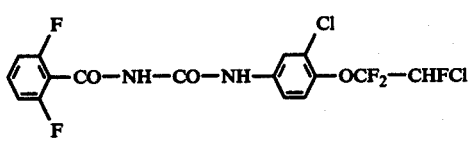

5. A urea according to claim 1 wherein such compound is N-(4-trifluoromethyoxy-phenyl)-N'-(2-chlorobenzoyl)-urea of the formula

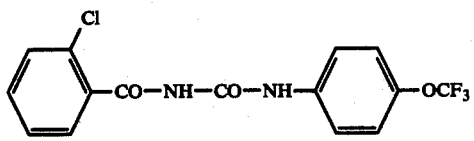

6. A urea according to claim 1 wherein such compound is N-(4-trifluoromethoxy-phenyl)-N'-(2,6-dichlorobenzoyl)-urea of the formula

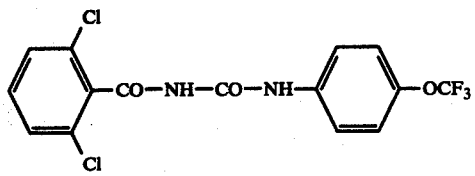

7. A urea according to claim 1 wherein such compound is N-(4-trifluoromethoxy-phenyl)-N'-(2,6-difluorobenzoyl)-urea of the formula

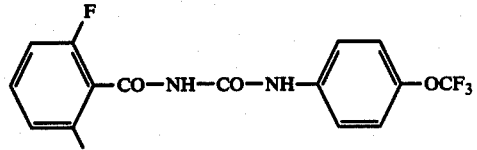

8. An arthropodicidal composition containing as active ingredient an arthropodicidally effective amount of a compound according to claim 1 in admixture with an agriculturally acceptable diluent.

9. A method of combating arthropods which comprises applying to the arthropods, or to a habitat thereof, an arthropodically effective amount of a compound according to claim 1.

10. The method according to claim 9 in which said compound is
- N-(4-trifluoromethylthiophenyl)-N'-(2,6-difluorobenzoyl)-urea,
- N-[3-chloro-4-(2-chloro-1,1,2-trifluoroethoxy)-phenyl]-N'-(2,6-difluorobenzoyl)-urea,
- N-(4-trifluoromethoxy-phenyl)-N'-(2-chlorobenzoyl)-urea,
- N-(4-trifluoromethoxy-phenyl)-N'-(2,6-dichlorobenzoyl)-urea or
- N-(4-trifluoromethoxyphenyl)-N'-(2,6-difluorobenzoyl)-urea.

* * * * *

Notice of Adverse Decision in Interference

In Interference No. 101,371, involving Patent No. 4,139,636, W. Sirrenberg, E. Klauke, I. Hammann and W. Stendel, N-PHENYL-N'-BENZOYL-UREAS AND PESTICIDAL COMPOSITIONS AND USES THEREFOR, final judgment adverse to the patentees was rendered Feb. 7, 1986, as to claims 1-10.
[*Official Gazette June 17, 1986.*]